United States Patent [19]

Heckler

[11] 4,343,799
[45] Aug. 10, 1982

[54] USE OF DERIVATIVES OF 6α-METHYLPREDNISOLONE FOR THE PREVENTION OR REDUCTION OF ADRIAMYCIN-INDUCED CARDIOTOXICITY

[75] Inventor: Jay W. Heckler, Kalamazoo, Mich.

[73] Assignee: The Upjohn Company, Kalamazoo, Mich.

[21] Appl. No.: 245,575

[22] Filed: Mar. 20, 1981

[51] Int. Cl.³ .............................................. A61K 31/56
[52] U.S. Cl. ................................................... 424/243
[58] Field of Search ................................ 424/181, 243

[56] References Cited

U.S. PATENT DOCUMENTS 2,897,218  7/1959  Sebek et al. ................... 260/397.4 S
3,193,459  7/1965  Korman et al. ...................... 424/243

Primary Examiner—Elbert L. Roberts
Attorney, Agent, or Firm—Sidney B. Williams, Jr.

[57] ABSTRACT

Use of water soluble 21-polybasic esters of 1-dehydro-6α-methylhydrocortisone and their salts for the prevention and treatment of cardiotoxicity induced by Adriamycin chemotherapy.

8 Claims, No Drawings

USE OF DERIVATIVES OF 6α-METHYLPREDNISOLONE FOR THE PREVENTION OR REDUCTION OF ADRIAMYCIN-INDUCED CARDIOTOXICITY

DESCRIPTION

BACKGROUND OF THE INVENTION

1. Field of the Invention

This invention relates to a method of using water soluble 21-polybasic esters of 1-dehydro-6α-methylhydrocortisone and their salts for the prevention and reduction of cardiotoxicity induced by doxorubicin (Adriamycin) chemotherapy. Adriamycin, an anthracycline antibiotic, is a broad spectrum antitumor agent that has been used in chemotherapy for over ten years. However, one of the most serious problems in the administration of Adriamycin in the treatment of cancer is the cardiotoxicity caused therapy.

A patient suffering from cardiotoxicity experiences prolonged systolic time interval (decreased frequency of heart beat) and/or increased resistance to coronary flow. Either of these toxic conditions can lead to severe heart damage and even death.

2. Description of the Prior Art

1-Dehydro-6α-methylhydrocortisone (6α-methylprednisolone) is a known pharmaceutical for treating inflammation. It has the following formula:

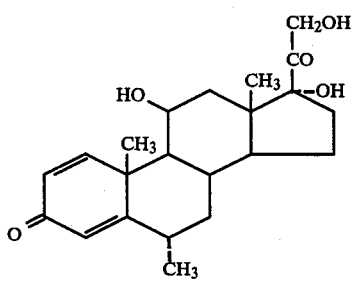

Water soluble 21-polybasic esters of 1-dehydro-6α-methylhydrocortisone, their salts and methods for preparing them are described in U.S. Pat. No. 2,897,218.

Bristow et al., Proc. AACR/ASCO 1979;20:118 discloses that histamine and catecholamines have been used to mediate cardiotoxicity resulting from the use of Adriamycin in chemotherapy. However, insofar as Applicant knows, water soluble 21-dibasic esters of 1-dehydro-6α-methylhydrocortisone and their salts have never been used as an aid to prevent cardiotoxicity induced by Adriamycin chemotherapy.

SUMMARY OF THE INVENTION

The method of this invention comprises treating patients undergoing Adriamycin chemotherapy with water soluble 21-dibasic esters of 1-dehydro-6α-methylhydrocortisone and their salts in an amount that is equivalent to from 125 mg to 2 grams of 1-dehydro-6α-methylhydrocortisone on the day in which chemotherapy is undertaken.

DETAILED DESCRIPTION OF THE INVENTION

In accordance with the manner and process of using the present invention, water soluble 21-dibasic esters of 1-dehydro-6α-methylhydrocortisone and their salts are administered intravenously to mammals and animals to prevent Adriamycin cardiotoxicity. An especially effective compound for use in the process of this invention is 1-dehydro-6α-methylhydrocortisone 21-hemisuccinate sodium salt (6α-methylprednisolone 21-succinate sodium salt).

The water soluble 21-dibasic esters of 1-dehydro-6α-methylhydrocortisone and their salts can be prepared by methods known in the art. U.S. Pat. No. 2,897,218 discloses such a method. The essential material constituting a disclosure of how to prepare and formulate said esters and salts is incorporated here by reference from U.S. Pat. No. 2,897,218.

The water soluble 21-dibasic esters of 1-dehydro-6α-methylhydrocortisone and their salts can be formulated for use in sterile intravenous solutions by methods that are conventional in the art.

The formulation as prepared can be administered in varying dosages depending upon the weight of the mammal under treatment. In the case of humans the daily dosage ranges from 125 mg to 2 grams. The preferred regimen of administration is a single dose.

The following Example is illustrative of the method of this invention, but is not to be construed as limiting.

EXAMPLE 1

Enough formulation containing 1-dehydro-6α-methylhydrocortisone 21-hemisuccinate sodium salt, as the active ingredient, to prepare 1000 8 ml vials, each containing the equivalent of 500 mg of methylprednisolone is prepared from the following types and amounts of ingredients.

| | |
|---|---|
| 1-Dehydro-6α-methylhydrocortisone 21-hemisuccinate sodium salt (equivalent to 500 mg/vial of 1-dehydro-6α-methylhydrocortisone itself) | 663 grams |
| Sodium Biphosphate, Anhydrous | 6.4 grams |
| Dried Sodium Phosphate | 69.6 grams |
| Benzyl Alcohol | 66.8 grams |

Sterile intravenous solutions of the prepared formulations can be prepared by mixing the content of a vial with 8 ml of bacteriostatic water.

Sterile solution is administered as follows, to prevent Adriamycin induced cardiotoxicity. One vial one-half hour before chemotherapy is started.

Other 21-polybasic esters of 1-dehydro-6α-methylhydrocortisone and their salts can be used to prepare formulations that can be used in the method of this invention. They include:

- 1-dehydro-6α-methylhydrocortisone 21-hemisuccinate phenylephrine salt
- 1-dehydro-6α-methylhydrocortisone 21-hemisuccinate N-methyl-glucamin salt
- 1-dehydro-6α-methylhydrocortisone 21(α,β-dimethylglutamate)
- 1-dehydro-6α-methylhydrocortisone 21-glycolate
- 1-dehydro-6α-methylhydrocortisone 21-tartrate and the sodium, phenylephrine, and N-methyl-glucamin salts thereof.

I claim:

1. A method for the prevention of Adriamycin-induced cardiotoxicity which comprises administering intravenously to a patient expecting Adriamycin chemotherapy, a formulation comprising a compound selected from the group consisting of water soluble 21- dibasic esters of 1-dehydro-6α-methylhydrocortisone and their salts in a pharmaceutically acceptable carrier.

2. A method according to claim 1 wherein the compound is 1-dehydro-6α-methylhydrocortisone 21-hemisuccinate sodium salt.

3. A method according to claims 1 or 2 wherein the amount of compound administered is equivalent to 125 mg to 2 grams of 1-dehydro-6α-methylhydrocortisone.

4. A method according to claims 1 or 2 wherein the formulation is administered both prior to and subsequent to the administration of the Adriamycin.

5. A method for the reduction of Adriamycin-induced cardiotoxicity which comprises administering intravenously to a patient who has had Adriamycin chemotherapy, a formulation comprising a compound selected from the group consisting of water soluble 21-dibasic esters of 1-dehydro-6α-methylhydrocortisone and their salts in a pharmaceutically acceptable carrier.

6. A method according to claim 5 wherein the compound is 1-dehydro-6α-methylhydrocortisone 21-hemisuccinate sodium salt.

7. A method according to claim 6 wherein the amount of compound administered is equivalent to 125 mg to 2 grams of 1-dehydro-6α-methylhydrocortisone.

8. A method according to claims 6 or 7 wherein the formulation is administered both prior to and subsequent to the administration of the chemotherapeutic agent.

* * * * *